United States Patent [19]

Jones et al.

[11] Patent Number: 5,256,533
[45] Date of Patent: Oct. 26, 1993

[54] AS A PROBE OF SEROTONIN UPTAKE HARMALINE

[75] Inventors: B. Eric Jones, Huffman; Dianna A. Redburn, Houston, both of Tex.

[73] Assignee: Board of Regents, The University of Texas System

[21] Appl. No.: 494,727

[22] Filed: Mar. 16, 1990

[51] Int. Cl.$^5$ .............. C12Q 1/00; C12N 13/00; G01N 21/76
[52] U.S. Cl. ................................ 435/7.24; 435/4; 436/172; 436/503
[58] Field of Search ................ 435/4, 173; 436/172

[56] References Cited

PUBLICATIONS

Bartonicek (1971) Pharmacology, 5(1), 36-42 in Chem Abst 74, p. 205, Abst #11808y.
Gineln et al, (1983) Res. Commun. Chem, Pathol. Pharmacol. 41(2), 349-352, in Chem Abstr., 99(17), p. 429, Abst. #137789.
Goldstein et al, (1971) Proc. Nat. Acad Sci., USA, 68(8), 1742-1747, Snyder (1984) Science, 224, 22-31.
McGeer et al, (1987) "Molecular Neurobiology of the Mammalian Brain", pp. 319-347.
Airaksinen et al (1978a) Arzneimittelforsch., 28(1), Heft 1:42-46.
Airaksinen et al (1978b) Acta pharmacol. et toxicol., 43:375-80.
Airaksinen et al (1987) Pharmacol. and Toxicol., 605-8.
Airaksinen et al (1981) Med. Biol., 59:21-34.
Airaksinen et al (1981b) Med. Biol., 59:190-211.
Airaksinen et al (1984) Acta pharmacol. et toxicol., 55:380-85.
Blackwell, B. (1981) Drugs, 21:201.
Bosin et al (1985) J. Chromatogr., 341:287-93.
Briley et al (1979) Eur. J. Pharmacol., 58:347-48.
Briley et al (1980) Science, 209(11):303-305.
Bruning et al (1985) Eur. Biochem., 153:95-99.
Bukard et al (1977) Biochem. Pharmacol., 26:1303-6.
Canessa et al (1973) J. membrane Biol., 13:263-82.
Erecinska, M. (1987) Bio. Phrama., 36(1):3547-55.
Fuentes et al (1971) Neuropharmacology, 10:15-23.
Fuller, R. W. (1976) Life Sci., 19:625.
de la Torre et al (1976) Histochem, J., 49:81.
Fuller et al (1986) Life Sci., 38:409.
Gershon et al (1962) Archs. Int. Pharmacodyn. Ther., 135:31-56.
Glennon et al (1979) J. Med. Chem., 22:428.
Glennon, R. A. (1981) Life Sci., 29:861.
Hsu et al (1975) Res. Commun. Chem. Pathol. Pharmacol., 12:355.
Inoue et al (1983) Anal. Biochem., 132:468.
Langer et al. (1984) Eur. J. Pharmacol., 98:153.
Leonard, B. E. (1988) J. Clin. Psychiatry, 49:8.
Mandel et al (1974) Science 186:741.
Marcusson et al (1986) Molec. Pharmacol., 30:121.
Muller et al (1981) Pharm. Biochem. & Behavior, 14:694-99.
Redburn et al (1987) J. Neurosci., 7:319.
Paul et al (1981) Arch. Gen. Psychiatry, 38:1315-17.
Paul et al (1981) Life Sciences, 28:2753-60.
Paul et al (1980) Life Sciences, 26:953-59.
Rommelspacher et al (1978) J. Neurochem., 30:1573-78.
Rommelspacher et al (1984) Arch. Pharmac., 327:107-13.
Rommelspacher et al (1980) FEBS Letters, 109(2):209-12.
Rommelspacher et al (1985) J. Pharmac., 109:363-71.
Schoenenweid et al (1986) J. Physiol., 81:19-25.
Sepulveda et al (1973) Biochemica et Biophysica Acta, 373:527-31.

(List continued on next page.)

Primary Examiner—Douglas W. Robinson
Assistant Examiner—Jon P. Weber
Attorney, Agent, or Firm—Arnold, White & Durkee

[57] ABSTRACT

Beta carbolines are naturally occurring fluorescent analogues of several classes of neurotransmitters, namely indoles, indoleamines and catecholamines. The fluorescent properties of the beta carboline, harmaline, has been used to assess serotonin uptake systems by direct visualization. This method may provide a tool to examine the mode of action of new or existing serotonergic active compounds or the efficacy of a serotonergic active compound for individual patients in need thereof.

2 Claims, 4 Drawing Sheets

PUBLICATIONS

Sklar et al (1984) *J. Bio. Chem.*, 259(9):5661–9.
Sneddon (1973) *Prog. Neurobiol.*, 1:153–98.
Sheddon (1969) *Br. J. Pharmac.*, 37:680–88.
Sneddon (1971) *Br. J. Pharmac.*, 43:834–44.
Stahl (1985) *Pharmacol. Bulletin*, 21(3):663–71.
Susilo et al (1987) *Arch. Pharmac.*, 335:70–6.
Thomas et al (1979) *Exp. Eye Res.*, 28:55–61.
Titus et al (1981) *Proc. Natl. Acad. Sci.*, 78:519–23.
Stanley et al (1981) *Science*, 216(18):1337–39.
Wyatt et al (1975) *Science*, 187:853–55.
Wirz-Justice (1988) *Experientia*, 44:145–52.
Gershon et al (1962) *Arch. Int. Pharmacodyn.*, CXXXV(1-2):31–56.
McKenna et al (1984) *Journal of Ethnopharmacology*, 10:195–223.
Schultes et al eds, *The Botany and Chemistry of Hallucinogens* (1973): pp. 106–111.
Schultes et al eds. *Plants of the Gods*, McGraw-Hill Book Company, Publishers, (1979):53.
Goldstein, R. S. and Camhi, J. M. (1991), *J. Comp. Physiology*, 168(1):103–112.
Botez et al. (1991), *Brain*, 114 (pt. 1A):333–348.
Inoue et al. (1991), *J. Cereb. Blood Flow Metab.*, 11(2):242–252.
PCT International Search Report.
SU, A, 859889 (Chitinsk Medical Institute) Oct. 1, 1981.
Progress in Chemical Biological Research, vol. 90, 1982, Alan R. Liss, Inc., New York, N.Y., U.S., N. S. Buckholtz: Interaction of tetrahydro-beta-carbolines with brain serotonin-based metabolism, pp. 183–190.
SU, A 1532867 (Lengd Vaccine Serum) Dec. 30, 1989.
Investigative Ophthalmology and Visual Science, vol. 31, No. 4, May 29, 1990 (Florida, US) B. E. Jones et al. "Harmaline: a physiologic probe for the indole systems in photoreceptor cells", p. 335, abstract.
N. S. Buckholtz (1982), *In: Progress in Chemical Biological Research*, 90:183–190.

HARMALINE AS A PROBE OF SEROTONIN UPTAKE

The Federal Government may have rights concerning the present invention in view of related research supported by research grants from the United States DHHS, NIH, (EY07024 and EY01655).

BACKGROUND OF THE INVENTION

Beta carbolines are complex heterocyclic structures with specific side groups attached at various points, differentiating members of this class of compound. The skeleton ring structure of beta carbolines consists of an indole group attached to a cyclic amine (FIG. 1). This structure has numerous conjugated double bonds which impart color to the compound via light absorption and emission spectra. Upon stimulation of these compounds with ultraviolet light, strong fluorescence is produced. Quantitative analysis utilizing the ultraviolet and fluorescent spectra of beta carboline has been shown to be accurate and sensitive (Bosin and Jarvis 1985; Inoue et al. 1983).

Alternate terms for beta carbolines found variously in the current scientific literature include:
Norharmane = beta-carboline (basic parent molecule)
Harman = harmane
Harman = 1-methyl-beta-carboline
Harmine = 7-methoxy-1-methyl-beta-carboline
Harmalol = 7-hydroxy-beta-carboline
Harmalan = 1-methyl-3,4-dihydro-beta-carboline
Harmaline = 7-methoxy-3,4-dihydro-beta-carboline
Pinoline = 6-methoxy-1,2,3,4-tetrahydro-beta-carboline
Tetrahydroharmane = 1-methyl-1,2,3,4-tetrahydro-beta-carboline
Tetrahydroharmane = 1-methyl-tetrahydro-beta-carboline
Tetrahydroharmane = tetrahydroharman
Tetrahydronorharmane = 1,2,3,4-tetrahydrobeta-carboline
Tetrahydronorharmane = "tryptoline"
Tetrahydronorharmane = tetrahydro-beta-carboline
Tetrahydronorharmane = tetrahydronorharman.

As noted above these beta carbolines have individual names, i.e., harmaline, harmane, etc., indole alkaloids, harmala alkaloids, and rarely seen older terms such as tryptolines and pyridoindoles. For purposes of the present invention the term "beta carboline" is intended to include the above listed compounds and any related compounds useful as vital stains for neurological tissue.

The basic beta carboline structure bears resemblance to endogenous indoleamine neurotransmitters, namely tryptamine, serotonin, melatonin, and others. The indoleamine structure consists of an indole heterocyclic group with various amine and hydroxyl groups attached. The beta carboline molecule is also structurally similar to the norepinephrine receptor blocker yohimbine and to a lesser degree, beta carbolines resemble catecholamine neurotransmitters, e.g., epinephrine, norepinephrine, and dopamine.

Naturally occurring beta carbolines have been isolated from plants and animals. A number of alkaloid beta carboline derivatives have been extracted from plants, each with variations on the number of double bonds present on ring 3 and side groups on ring 1 (FIG. 1) (Glennon 1981). These plant extracts (harmala alkaloids) have experimentally been found to interact with neurotransmitter systems (Rommelspacher 1978). FIG. 1 also schematically shows the structure of indole; serotonin; harmol; harmine; harmalol; and harmaline.

Researchers have examined the interactions of these compounds with the serotonergic systems within the brain. Various beta carbolines have been found to antagonize serotonin receptors. (Glennon 1979). Harmaline is one beta carboline which has a high binding affinities for serotonin receptors. (Glennon 1981). The precise biochemical mechanism of serotonin antagonism by harmaline is only partly clarified. Harmaline is known to block cell membrane uptake of serotonin as well as receptor binding (Airaksinen et al. 1981). Some researchers have accounted for this by interaction of beta carbolines with an "imipramine receptor," the site at which tricyclic antidepressants bind and inhibit serotonin uptake (Airaksinen et al. 1978; Langer et al. 1984).

In addition to interactions with serotonin sites, beta carbolines are known to inhibit a number of other neurological binding sites. For instance, harmine and other related beta carbolines exhibit potent interactions with the benzodiazepine receptor (Rommelspacher et al. 1981) as well as known endogenous neurotransmitter receptors for acetylcholine, opiate, serotonin, and dopamine sites. One study has shown that the $IC_{50}$ (concentration required to inhibit 50% of binding) value of Harmaline for opiate and muscarinic cholinergic sites was about four times lower than for serotonin or dopamine sites, but, in contrast, was about four times higher than found for benzodiazepine antagonism (Muller et al. 1981). Accordingly, Harmaline is a far more potent antagonist of benzodiazepine binding than it is for serotonin or dopamine.

In vivo studies of the effects of beta carbolines in animals support the in vitro findings of various selective neurological interactions. Harmine and some other related beta carbolines having effects not unlike a benzodiazepine antagonist would e.g., increased anxiety, CNS stimulation, and convulsions (Sigg et al. 1964; Gershon and Lang 1962; Fuentes and Longo 1971). Still other in vivo effects, psychotomimetic, tremorigenic or antipsychotic, support the findings that these compounds interact with cholinergic and serotonergic receptors as well. In addition to these interactions, various beta carbolines have been experimentally shown to interact with noradrenaline and tryptamine receptor sites in neurological tissue (Airaksinen et al. 1984; Given and Longenecker 1983).

Beta carbolines can variously locate and assess the activity or presence of neurotransmitter accumulation sites. The various neurons and other cells which release the above neurotransmitters have transport mechanisms which reaccumulate the neurotransmitter for the purported purpose of conservative reprocessing and self regulation. Some beta carbolines have exhibited potent competitive inhibition of this "uptake" (Sepulveda and Robinson 1974). The present inventors have observed that beta carbolines accumulate in discrete areas of tissue known to be rich in these uptake sites and that this accumulation can be monitored and accurately measured via e.g., fluorescent microscopy or fluorescent flow cytometry. This measurement of a neurotransmitter analogue would effectively allow the measurement of neurotransmitter accumulation sites.

The interaction of beta carbolines with receptor and uptake sites has been shown to be reversible and nontoxic to metabolic processes at low doses with 100% recovery following their application (Schonenweid et al. 1981, 1986). Beta carbolines also antagonize the action of monoamine oxidase A, the enzyme responsible for the breakdown of serotonin (Blackwell 1981; Burkart and Kettler 1977). Harmaline has been shown to potently inhibit this intracellular enzyme in vivo (Fuller et al. 1985).

The use of this group of compounds would allow the monitoring of a variety of neurotransmitter activities in living tissue. To measure the activity of receptor and uptake sites of a specific neurotransmitter, a beta carboline with a high specificity may be used. Alternatively, a pretreatment with various known neurotransmitter blocking agents (non-fluorescent) to block undesired interactions may also be employed. With the use of various pretreatment solutions followed by application of the beta carboline vital stain, the measurement of the varied aforementioned neurotransmitters would be possible.

The activity of serotonin, norepinephrine, acetylcholine, dopamine, opiate, tryptamine, and benzodiazepine systems play a significant role in many psychiatric disorders. For example, serotonin receptor number and uptake site activity changes in the pathological states of schizophrenia, depression, suicidal behavior, and others (Stahl et al. 1985). For patients with major affective depression, drugs which alter the uptake site activity of norepinephrine and serotonin, "tricyclic antidepressants" offer the mainstay of effective treatment. No generally effective method for the accurate assessment of these sites needed for the diagnosis and more importantly the effective management of these patients currently exists.

In an attempt to treat patients suffering from the above psychiatric disorders, physicians have administered tricyclic antidepressants and other neurologically active compounds to their patients. Tricyclic antidepressants are a class of psychopharmacological agents which interact with serotonergic and other neurotransmitter systems. It is believed that the action of the tricyclic antidepressants is to inhibit the re-uptake, and thus the metabolism of catecholeamines and indoleamines. Though the mechanism of action of this class of drugs is not completely elucidated, they are thought to induce a delayed uptake of the neurotransmitter at the postsynaptic receptor and thus the effect of the neurotransmitter. For example, all tricyclic antidepressants block the re-uptake of norepinephrine by adrenergic nerve cells. Nevertheless, each tricyclic antidepressant affects each neurotransmitter system in a distinctly different way, thus eliciting distinctly different responses in patients. For instance, imipramine slows the turnover rate of 5-hydroxytryptophan, an effect not shared by desipramine, while the turnover rate of norepinephrine is increased by the demethylated drugs nortriptyline and desipramine. The exact relationship of these effects to the action of the tricyclic antidepressants in human depression is not known. Therefore, it would be advantageous to provide a method useful in defining the mechanism of action of tricyclic antidepressants and other psychoactive compounds in order to better understand and treat patients suffering from these pathologies.

The treatment of patients with psychiatric disorders has usually been limited to the administration of psychopharmacological agents. The selection of a particular psychopharmacological agent is often based on the outward manifestations of the patient. For example, clinical rating scales for qualifying symptom complexes are available to define treatable target symptoms on the basis of clinical interviews and observations. However, because these drugs often elicit different effects in different patients, the choice of drug is often not based on anticipated therapeutic effect, but on the side effects of the particular drug and the patient's history using the drug. If a patient has responded well to a drug in the past, it is typically used again; if the patient's history does not indicate either a drug of choice or one to be avoided, clinical guidelines have been established for selecting and administering an agent. Generally, these guidelines consider the side effects of the drug, patient compliance, sedative effect of a drug, and general medical condition of the patient. Further, the choice of a particular drug is also conditioned on the physician's experience with the particular drug, a factor that often outweighs all others.

The effective use of these drugs also depends on the selection of an adequate dosage level. Typically, the tricyclic antidepressants are administered initially with a single dose at bedtime and increasing to a total daily dose by the end of the first week. If the patient shows no response in the first two weeks, the dose can be increased to a maximum allowable dosage. If the patient does not respond to one tricyclic antidepressant compound, another may be substituted. If the patient is unresponsive or unmanageable, electroconvulsive shock therapy may be necessary.

Some patients do not respond to psychopharmacological treatment and their disease may even worsen after treatment. Because "nonresponders" cannot be identified beforehand with certainty, the physician must accept the fact that there is a small subgroup of patients who do worse on medication than on no medication at all. The reported percentages of patients showing improvement with tricyclic drugs varies widely from about 32 to about 80%, depending on the criteria used for diagnosis and improvement. However, most psychiatrists report improvement in approximately 60 to 70% of depressed patients. It has been postulated that a disorder of amine metabolism exists in some depressed patients. Presumably, it is these patients who respond favorably to antidepressant drugs. A disorder of amine metabolism may also afflict some patients with mania. Accordingly, it would be advantageous to provide a method useful in identifying those patients who would respond favorably to psychopharmacological treatment, and more particularly, to provide a method useful in identifying the particular psychopharmaceutical agent to which a patient suffering from a psychiatric disorder would favorably respond.

As discussed above, the effective treatment of patients with psychopharmacological agents depends upon the dosage administered to the patient. Dosage is generally determined by the outward manifestations of the patient, the blood levels of the drug administered, or the breakdown products of neurotransmitter metabolism. Serotonergic receptor number and uptake site activity change in several psychiatric disorders. It is believed that psychopharmacological agents elicit their effect by interacting with these neurotransmitter systems. Ideal blood levels of psychopharmacological agents are often misleading, if not worthless, because of such changes. As previously discussed, a large percentage of patients are nonresponsive to psychopharmacological agents, regardless of their corresponding blood level. In the past, breakdown products of neurotransmitter metabolism have been measured in the blood, urine and cerebrospinal fluid to follow the progress of a patient's treatment. However, examining catabolites of neurotransmitters is an indirect method which may be influenced by several factors, particularly in a system modulated by psychopharmacological treatment. Thus, presently there is no method for accurately determining the dose of a psychopharmacological agent necessary to treat a patient suffering from a psychiatric disorder. Accordingly, it would be advantageous to provide a method to measure the activity of neurotransmitter uptake sites which are, in fact, the target of tricyclic antidepressant and other psychopharmacological agents. Further, it would be advantageous to provide a vital stain for neurotransmitter systems which could be utilized to determine the activity of neurotransmitter uptake sites in a patient. Thus, optimum drug dose could be predicted for individual patients depending on their unique physiology. A beta carboline used as described above would advantageously provide researchers with a tool for understanding psychiatric disorders, choosing particular psychopharmacological agents useful in the treatment of psychiatric disorders, and selecting an effective dosage of a psychopharmacological agent for a patient in need thereof. In addition, this method of assessing the activity of neurological systems may provide medicine with the first effective objective test with which to diagnose schizophrenia.

Because of the inaccessibility of brain tissue, many of the receptor and uptake sites of interest are impractical to analyze. However, lymphocytes and platelets are alternative tissue sources that contain serotonin uptake and receptor sites (Stahl et al. 1985). Human platelets are perhaps the best developed peripheral model and the most extensively studied. They are rich in serotonin receptors and uptake sites (Stahl and Meltzer 1978; Sneddon et al. 1969, 1971, 1973; paul et al. 1980, 1981a) as well as imipramine binding sites (Briley et al. 1979) (some authors have hypothesized a closely associated but separate receptor for serotonin and imipramine, a potent pharmacologic serotonin uptake inhibitor, while other authors present a single site model). Platelets, like lymphocytes, have monoamine oxidase, alpha-2 adrenergic receptors, and Na/K ATPase. In addition lymphocytes are rich in beta-adrenergic receptors. The receptor/uptake systems of platelets and of central nervous system have been suggested by others to be analogous in view of the many demonstrated similarities.

For instance, in major depressive disorders the capacity and number of serotonin uptake sites is decreased in platelets as well as in central nervous system tissue (Justice et al. 1988; Briley et al. 1980: Paul et al. 1981b; Stanley et al. 1982). Fluorescent cell sorting (Flow cytometry) is a recognized tool which, through recent developments, can measure kinetics of bound and unbound ligands in equilibrium using fluorescent labeling techniques. Lymphocytes and platelets are particularly amenable to study with the present methods. Another method, spectrofluorometry, may be used to evaluate the total amount of fluorescence given off from a solution. Though this peripheral model of neurological tissue is relatively new, it has gained wide acceptance. With the availability of fluorescent neurotransmitter analogues which can stain unfixed tissue, together with accurate methods to analyze staining, this method of investigating the nervous system should contribute significantly to the development and effective use of psychoactive drugs.

SUMMARY OF THE INVENTION

One aspect of the present invention is directed to the use of beta carboline compounds as non-toxic vital stains or markers for intracellular pools of serotonin or other neurotransmitters in living tissue. Accordingly, a method is provided for fluorescently staining intracellular reservoirs of neurotransmitters in mammalian tissue. The inventive method includes the steps of:
a. obtaining viable cells;
b. treating said cells with a beta carboline;
c. irradiating said treated cells with ultraviolet light; and
d. observing fluorescence from said irradiated cells, said fluorescence being indicative of neurotransmitter receptor or storage sites.

Areas of concentrated fluorescence correspond to neurotransmitter reservoirs. Tests of the present invention have established that beta carbolines are accumulated by the serotonergic neurotransport system in peripheral blood cells, e.g., leukocytes and platelets, and retinal neurons.

Another aspect of the present invention is directed to a method for evaluating the functioning of a neurotransmitter system in a mammal. The method includes the steps of:
a. adding a quantity of a beta carboline to a mammalian tissue sample with a functioning neurotransmitter system, said beta carboline accumulating in the functioning neurotransmitter system of said sample; and
b. fluorescently imaging the sample, wherein areas of concentrated fluorescence correspond to reservoirs of beta carboline accumulated by the functioning neurotransmitter system.

Tests of the present invention have determined that both the rate and quantity of the beta carboline taken up by the neurotransmitter system are indicative of the functioning of this transport system. The present inventive method should be clinically useful in detecting those patients which will not benefit from psychopharmaceutical therapy. In this method or that of the prior paragraph, a step may be inserted just prior to step b) to pretreat the tissue with agents which block any undesired localization of the beta carboline.

A further aspect of the present invention is a method to determine the likely efficacy of a particular psychopharmacological agent in an individual to be treated or being treated with the agent. This method includes the steps of:
a. obtaining from a mammal a viable tissue sample comprising a functional neurotransmitter system;
b. adding a pharmacologic neurotransmitter agonist or antagonist to the tissue sample;
c. adding an amount of a beta carboline which labels the functional neurotransmitter system;
d. fluorescently imaging the tissue sample, wherein areas of concentrated fluorescence correspond to reservoirs of beta carboline accumulated by the neurotransmitter system; and
e. comparing quantity or rate of the beta carboline fluorescent labeling to control values obtained without presence of neurotransmitter agonist or antagonist or to control values separately determined, wherein an effective level of the neurotransmitter agonist or antagonist significantly decreases areas or intensity of beta carboline fluorescent labeling.

A still further aspect of the present invention is directed to a method for determining the optimum dosage of a particular psychopharmaceutical agent to be administered to an individual in need thereof. The method comprises the steps of:

a. adding to a tissue sample from an individual, neurotransmitter agonists or antagonists which block undesired localization of beta carboline;
b. interacting the sample with a proposed or standardized psychopharmacologic agent used to affect the neurotransmitter system;
c. adding a quantity of a beta carboline which accumulates in the neurotransmitter system;
d. fluorescently imaging the tissue sample, wherein areas of concentrated fluorescence correspond to reservoirs of beta carboline accumulated; and
e. comparing beta carboline images to those obtained from a tissue sample obtained when step (b) is omitted.

It is believed that this method will be useful in predicting the clinical effectiveness of a particular dosage of a currently available tricyclic antidepressants or other psychopharmaceutical agents in individual patients. In addition, the inventive method should be useful in helping to elucidate the mechanism of action of certain drugs already in use.

Many "tricyclic" or "heterocyclic" antidepressants are currently in use for a range of psychopathologies in addition to depression, including narcolepsy, obsessive compulsive disorders, panic and phobic disorders, as well as more somatic/organic disorders including peptic ulcer disease, postherapeutic neuralgia and diabetic neuralgias. Though the effectiveness of many such drugs in selected cases is agreed upon, the mechanism of action in depression and in these varied diseases is not, despite the large body of data that has accumulated. One interesting phenomena produced by these drugs is a tardive mood altering effect taking 10 to 14 days after adequate blood levels are achieved. It has been argued that this indicates the effects are not due to the drugs administered, however innumerable double blind placebo/drug studies confirm the effectiveness of these drugs.

To elucidate the exact mechanism of these drugs, a nontoxic method to investigate activity of uptake systems (energy dependant) under drug influence over time would be most advantageous. Also the accumulation of the beta carboline under ideal conditions could be compared to accumulation in fixed (dead) or energy free (0-4 degrees centigrade) tissue to examine uptake system accumulation vs. receptor binding of the beta carboline only. In addition to this research application, a practical use of beta carbolines toward patient management is also envisioned. As the effectiveness of a particular dose and type of antidepressant is not known for 10 to 14 days in many instances, extended hospital stays are not infrequent as the dose and type of antidepressant are slowly titrated. A method whereby the effectiveness of a particular drug and dose can be ascertained before the patient is given a drug would be important not only to the patient and the hospital, but to the research of the mechanism of action of these drugs in general.

In addition to antidepressants there are a multitude of other drugs which act on or have effects because of interactions with neurotransmitter systems. With many of the various drugs currently in use, the varied mechanisms of action are as yet not all completely elucidated. The description of the action of antidepressants is therefore only an example of many classes of drugs and their associated neurotransmitter systems. Other examples might include the psychopathology of psychosis, involving the varied phenothiazine drugs and the dopamine system; Parkinson's disease and other movement disorders, involving anticholinergic drugs and the balance of the dopamine/choline systems, and others.

DESCRIPTION OF THE PREFERRED EMBODIMENTS

This invention generally relates to methods which utilize beta carbolines as vital stains or markers for neurotransmitter systems. Tests of the present invention have determined that beta carbolines are selectively taken up and stored by functioning neurotransmitter systems. Beta carbolines are strongly fluorescent compounds and, when excited by ultraviolet radiation, emit visible light. Therefore, the selective accumulation of a beta carboline within a living tissues may be visualized.

Figure 1:
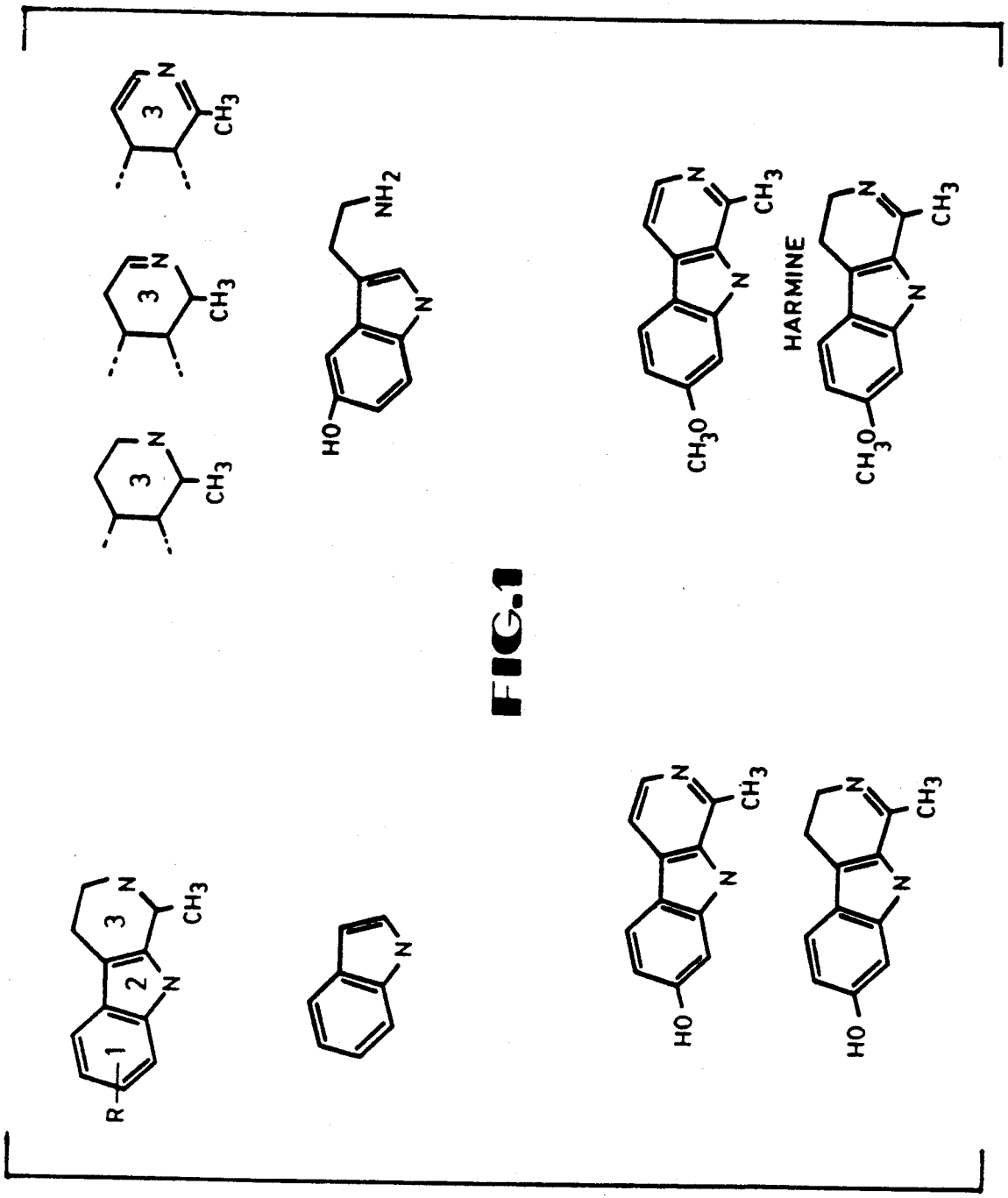
FIG. 1 schematically shows structures of beta carbolines, serotonin, specific harmala alkaloids and related structures.
Figure 2:
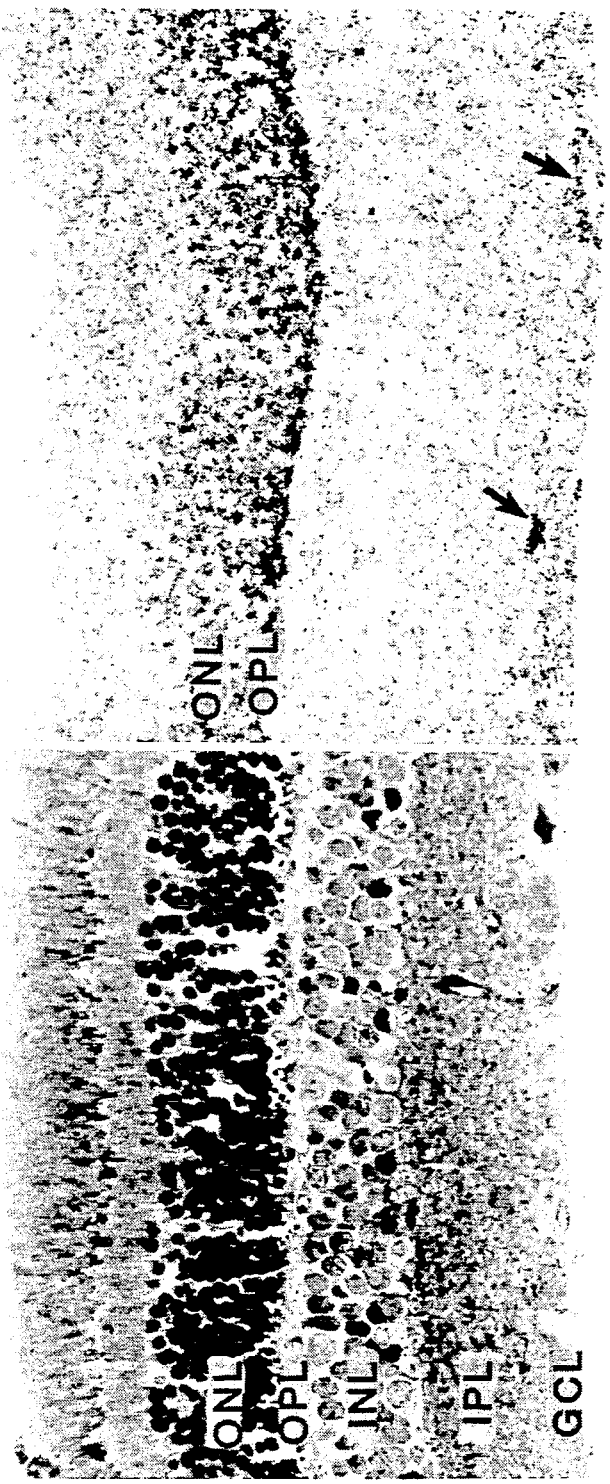
FIGS. 2A and B show ($\times 375$) localization of serotonin in rat retina using $^3$H-serotonin autoradiography - 2A, isolated retina showing normal morphology. ONL, Outer nuclear layer; OPL, outer plexiform layer; INL, inner nuclear layer; IPL, inner plexiform layer; GCL, ganglion cell layer. 2B, isolated retina incubated in $^3$H-serotonin showing specific accumulation of label in the OPL and perhaps in the ONL. Arrows denote labeled vascular elements.

Serotonin accumulation in retina has been localized via autoradiographic studies (using $^3$H-serotonin) and found to be associated with photoreceptor terminals, particularly in the outer plexiform layer (FIG. 2). This specific uptake of $^3$H-serotonin is sensitive to light conditions during incubation periods. After 20 minutes in darkness, no accumulation of isotope is appreciated (Redburn and Churchill 1987). This uptake is also sodium and temperature dependent. By understanding some of the regulatory physiology of this system, one can better approach the fate of serotonin, and consequently the expectations of harmaline as a neurotransmitter analogue.

TABLE 1 illustrates the general inhibitory effects of beta carbolines on neurotransmitter binding by brain tissue. Samples of brain tissue rich in the respective neurotransmitter binding sites were obtained, homogenized, washed and incubated with a series of beta carboline concentrations. After subsequent additions of tritiated neurotransmitters, the extent of beta carboline inhibition of labeled neurotransmitter binding was measured. As shown, a variety of beta carbolines were effective antagonists of several neurotransmitters. $IC_{50}$ values indicate concentrations of the indicated beta carboline which causes a 50% inhibition of the respective neurotransmitter isotope binding with brain homogenates. These data indicate binding preferences of the beta carbolines shown. These beta carbolines may be used as vital stains for the respective neurotransmitter systems, accumulating in living tissue.

TABLE 1

Inhibition of Neurotransmitter Binding by Beta Carbolines

| | $^3$H]Serotonin | [$^3$H]Choline |
|---|---|---|
| 7-methoxy-3,4-dihydro-beta-carboline (harmaline) | $4.3 \times 10^{-5}$ | — |
| 1,2,3,4-tetrahydro-beta-carboline | $6.0 \times 10^{-6}$ | $9.0 \times 10^{-3}$ |
| 7-methoxy-1-methyl-beta-carboline | $2.7 \times 10^{-5}$ | $2.0 \times 10^{-4}$ |
| beta-carboline | $9.1 \times 10^{-6}$ | $7.5 \times 10^{-5}$ |
| 1-methyl-beta-carboline | — | $8.5 \times 10^{-5}$ |

| [$^3$H]GABA | [$^3$h]Noradrenaline | [$^{14}$C]Dopamine |
|---|---|---|
| $23.8 \times 10^{-5}$ | $4.3 \times 10^{-5}$ | — |
| $15.3 \times 10^{-5}$ | $1.3 \times 10^{-5}$ | $2.2 \times 10^{-4}$ |
| — | $7.0 \times 10^{-4}$ | |
| $33.5 \times 10^{-5}$ | $8.0 \times 10^{-5}$ | $1.0 \times 10^{-14}$ |
| $16.8 \times 10^{-5}$ | $4.4 \times 10^{-5}$ | — |

One aspect of the present invention is directed to the use of beta carbolines as non-toxic vital stains or markers for intracellular pools of serotonin or other neurotransmitters in living mammalian tissue. A method includes the steps of:

a. obtaining viable cells;
b. treating said cells with a beta carboline;
c. irradiating said treated cells with ultraviolet light; and
d. observing fluorescence from said irradiated cells, said fluorescence being indicative of neurotransmitter receptor or storage sites.

Areas of concentrated fluorescence correspond to neurotransmitter reservoirs. Tests of the present invention have established that harmaline, an investigated beta carboline that expresses a preference for serotonergic receptor and uptake site, is accumulated measurably in retinal neurons as well as blood tissues including leukocytes and platelets.

Once a desired neurotransmitter system for analysis is chosen, the appropriate fluorescent beta carboline is also selected which will interact with this neurotransmitter system. Antagonist(s) which will block undesired interactions are also chosen. An adequate amount of this blocking agent is added to the tissue prior to adding beta carboline and subsequent neurotransmitter evaluation.

For this experiment, the beta carboline, harmaline was used. This beta carboline exhibits strong fluorescence and interacts with the serotonin neurotransmitter system. Prior to the use of a beta carboline to analyze blood tissues, blood was collected, then leukocytes and platelets were gradient separated utilizing a hypaque/-centrifugation technique. The leukocytes were then re-suspended in culture media (phosphate buffered saline (PBS) with bovine serum albumin) at a concentration of $1 \times 10^6$ cells/mm$^3$. The cells and platelets may then be incubated with a solution containing antagonist(s) or blockers of undesired neurotransmitter interactions. With harmaline, there is some amount of cross reactivity with the alpha-2 (noradrenaline) receptor. As the blood cells and platelets both have alpha-2 receptors, the noradrenaline antagonist, yohimbine was chosen to block undesired reactivity with these sites. Cells were incubated for 10 minutes with a 100 $\mu$M solution of yohimbine. The cells were then divided into numerous samples which were each exposed to increasing concentrations of harmaline (1 $\mu$M to 100 $\mu$M concentrations were used) for a period of five minutes each. These cells were then treated with fixative to stop accumulation and/or release of harmaline and washed with PBS to clear any excess. The labelled cells were then analyzed using both spectrophotofluorometry and ultraviolet flow cytometry. With the flow cytometry-analyzed tissue an experiment to detect the presence of imipramine, the serotonin uptake system antagonist, was implemented.

In spectrophotofluorometry (SPF), a volume of labeled cells in suspension are analyzed together, the sum of their emitted fluorescence recorded using a spectrophotofluorometer and compared with other samples with the same concentration of cells. It is important with this technique to remove as much of the fluorescent beta carboline from the surrounding media (via washing with centrifugation) as possible before analyzing the cells. This method assumes that the fluorescence emitted from a sum of collected sources (cells) increases proportionally with an individual source. Using this method, an $EC_{50}$ value (concentration needed to obtain 50% of effect) of $3.0 \times 10^{-5}$ M was obtained with harmaline.

Preliminary data suggests that this may be an effective method of measuring changes in accumulation of beta carboline in a population of leukocytes and platelets. Harmaline, a beta carboline which exhibits a propensity for serotonergic sites was used in conjunction with human lymphocytes, reported to have serotonin receptors and uptake sites. A robust accumulation of the beta carboline was observed, particularly in the lymphocytes. Upon measuring the fluorescence, it was found that this accumulation is a saturable, concentration-dependant phenomena.

With flow cytometry, a sample of cells was treated prior to analysis, as above. Fluorescence of individual cells was then analyzed sequentially as they passed through detection beams of light in a micro-stream of fluid. Using this method, literally emissions of cells, or "events" were analyzed and statistically computed to elicit accuracy of analysis. In addition, as individual cells are analyzed, more subtle changes in fluorescence ligand-cell association can be appreciated. There are some procedures for measuring the actual number of binding sites on cells which combine flow cytometry with steady-state fluorescence (Steinkamp and Kramer 1979) or radiometric assays (Titus et al. 1981), while others employ fluorescent calibration standards (Sklar et al. 1984). With this widely accepted and utilized device available in many hospitals, it is possible to more accurately quantify, and determine the rate of, accumulation of fluorescent ligand in various solutions of cells or platelets exposed to beta carboline for various amounts of time.

In a preliminary investigation of the use of the flow-cytometer instrument with lymphocytes and platelets treated with a beta carboline, harmaline, positive results were obtained. Harmaline preferentially localizes at serotonergic sites as demonstrated by blocking with serotonin and with imipramine, and was measurably found to accumulate on both lymphocytes and platelets. This accumulation was found to be concentration dependant and exhibited saturation at 75-100 μM concentrations of harmaline at 5 minutes. An $EC_{50}$ value of $2.5 \times 10^{-5}$ M was obtained. In an experiment which only briefly incubated cells and platelets with imipramine (25 μM), a tricyclic antidepressant and serotonin uptake inhibitor, the measured harmaline accumulation was less. The ultraviolet light flow-cytometer should prove to be a most valuable instrument in the analysis of beta carboline accumulation on patient blood cells and platelets, and thus in the measurement of their neurotransmitter systems.

One step in the above method is obtaining a viable tissue sample comprising a functional neurotransmitter system. According to one preferred embodiment, the tissue sample is obtained by first removing a predetermined quantity of blood from an individual. The quantity of blood is subsequently processed to isolate the leukocytes or the platelets. It is the leukocytes or platelets which constitute the preferred tissue sample comprising the neurotransmitter system to be stained. Neurons or brain tissue itself may also be a tissue sample compromising a functioning neurotransmitter system. According to this embodiment, a sample of nervous tissue is biopsied and placed in a sustaining medium.

Another step in the inventive method is adding a quantity of a beta carboline to the tissue sample. Preferably, the beta carboline compound is added as an aqueous solution having to achieve a concentration of from about $2.5 \times 10^{-6}$ to about $2.5 \times 10^{-2}$ mg/ml (10 nM-100 μM). Particular useful beta carbolines include but are not limited to harmine, tetrohydroharmane, norharman, tetrahydronorharman, norharmane, and harmaline, with harmaline being a particularly preferred beta carboline useful in the practice of the present invention.

A further step in the present invention is fluorescent imaging of a tissue sample. When imaged the tissue sample is exposed to ultraviolet radiation having of a wavelength of from about 300 to about 500 nm (one particular useful wavelength being 370 nm). Instruments which may be used to image the tissue sample include a fluorescent microscope, a transmission spectrophotometer, an ultraviolet spectrophotometer, a spectrophotofluorometer and a flow cytometer with ultraviolet wavelength capability. However, the most preferred instrument to image the tissue sample, particularly in a clinical setting, is the flow cytometer. It is believed that an area of concentrated fluorescence is indicative of intracellular pools, or reservoirs, of neurotransmitters. Other modes of beta carboline labeling such as with a radioisotope, for example, may also be useful for the identification of neurotransmitter-related sites or alterations thereof.

It is believed that the beta carbolines of the present invention co-localize with endogenous neurotransmitters in intracellular pools. Thus, it is should be noted, that the most preferred beta carbolines of present invention are also non-toxic to cells and that their uptake and concentration is influenced by the same physiologic parameters as is the neurotransmitter of interest, e.g., serotonin, GABA or dopamine.

Tests according to the present invention include: 1) the investigation of the serotonin neurotransmitter system utilizing harmaline, a beta carboline purported to interact with serotonin sites somewhat selectively, and 2) investigation of the noradrenaline system using the beta carboline tetrahydronorharman, a beta carboline which has shown potent antagonism of the adrenergic system as well as less potent interaction with serotonin sites.

Figure 3:
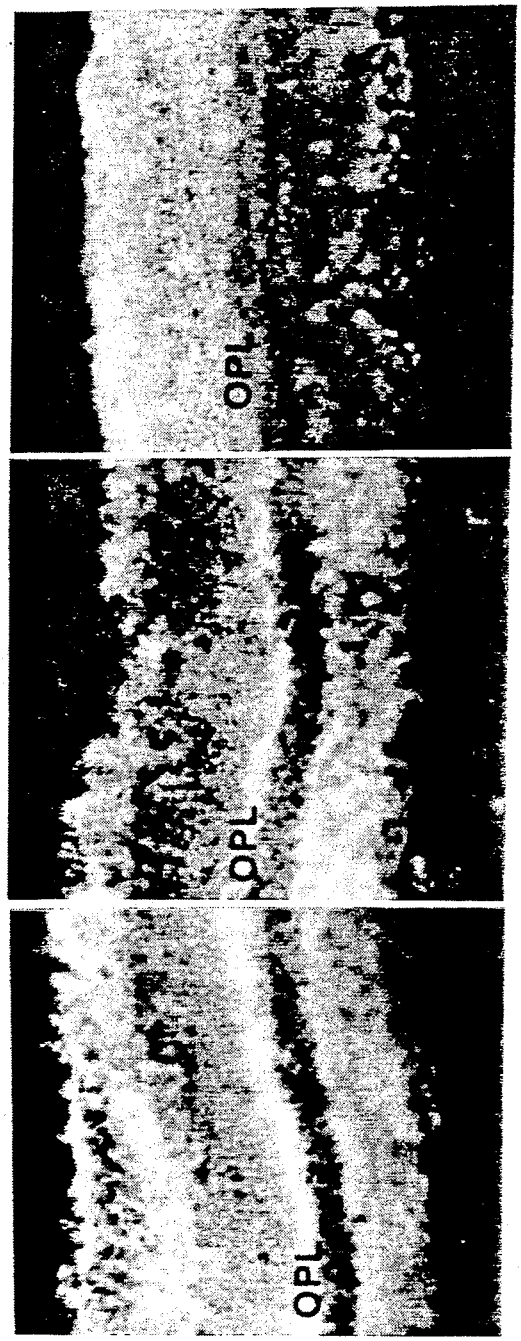
FIGS. 3A, B and C show ($225\times$) localization of fluorescent harmaline in rat retina. Frame 3A shows living retina stained with harmaline. Normal buffer perfusion solution is used throughout. Frame 3B shows retina stained with harmaline in normal buffer, then exposed to sodium-free buffer. Harmaline begins to disappear. Frame 3C shows retina stained with harmaline in normal buffer, then exposed to darkness (stimulating release).
Figure 4:
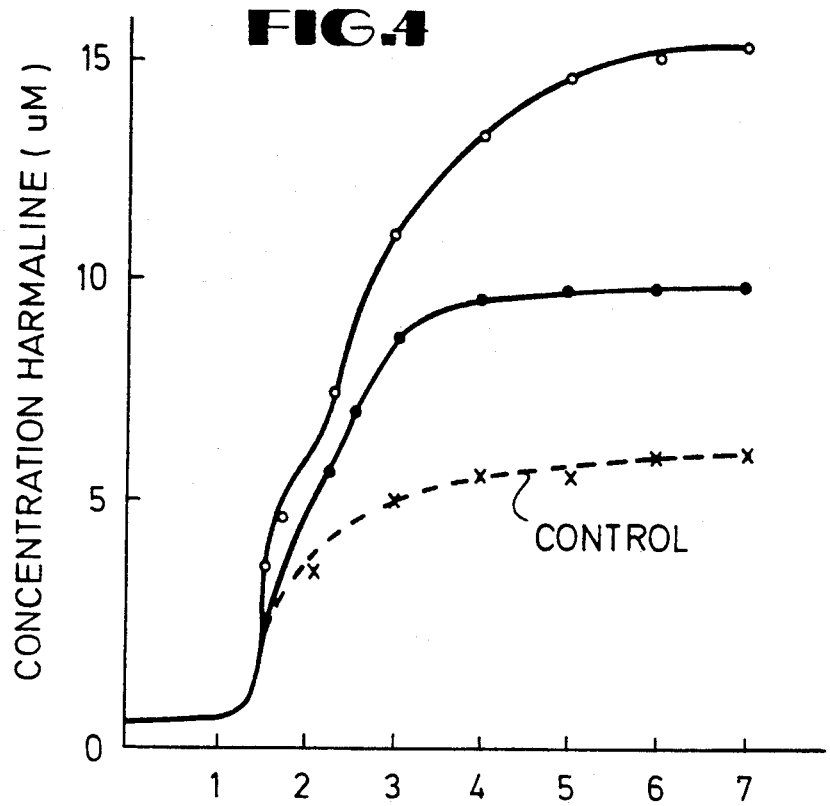
FIG. 4 shows the accumulation of harmaline in unfixed retina under light/dark conditions. Tissue was perfused with oxygenated Krebs buffer/5 $\mu$M harmaline.

One test of the serotonin site ligand, harmaline, is in the neuronal tissue of the rat retina. This tissue is known to contain intracellular serotonin. The serotonergic neurotransmitter system in rat retinal neurons has been previously studied and sites of serotonin accumulation have been identified (Redburn and Churchill 1987) primarily using radiolabelled $^3$H-serotonin (see FIG. 2). According to one test of the invention, it was determined that harmaline accumulated in living rat retina tissue in a specific manner. Fixed sections of rat retina treated with harmaline showed a band of fluorescence accumulated within the outer plexiform layer homologous to autoradiographs with $^3$H-serotonin shown in FIG. 2. Harmaline was found to accumulate initially in outer segments of photoreceptors. Later, fluorescence was observed in the soma of photoreceptor cells with a bright band of fluorescence accumulating in the outer plexiform layers (FIG. 3, frame A). The harmaline present in the OPL begins to dissipate when the stained retina is exposed to sodium-free buffer (see FIG. 3, frame B). Exposure of the stained retina to darkness stimulates harmaline release from the OPL (see FIG. 3, frame C). Further, quantitative evaluation of harmaline accumulation was achieved by measuring the amount of fluorescence given off by harmaline when excited with UV-radiation. A light meter was used to generate data. The light meter gathered light emissions from the eyepiece of an ultraviolet microscope. Harmaline's excitation spectrum is 350-390 nm with emission spectra greatest at 480 and 560 nm in the visible range producing a blue green light. Tissue was placed under a microscope in a sealed perfusion chamber through which oxygenated (95% $O_2$-5% $CO_2$) buffer flowed. Upon administration of harmaline, data from the light meter was standardized to units of harmaline concentration (using standard curves). With this apparatus it was found that the outer retina accumulated harmaline at a concentration 3 fold greater than the surrounding perfusate (perfusion concentration -5 μM harmaline) and 3 fold greater than control tissue (non-viable tissue). See FIG. 4.

Further, it was found that this accumulation was sodium dependent, energy dependent and led to accumulation three times greater inside than outside the cell. Harmaline made photoreceptor cells fluoresce with greatest concentrations in the outer plexiform layer at the photoreceptor terminals, demonstrating that harmaline provides a vital stain or marker for serotonergic transmitter pools.

The analysis of a noradrenaline system using the beta carboline tetrahydronorharman (THN) could be tested using the method described with blood cells and platelets. Cells and platelets would be collected, then pretreated with solutions to block sites of the serotonin system in order to limit interactions to that of the noradrenergic system. Cells would be first incubated for 10 minutes with the serotonin uptake blocker, imipramine at 100 μM, following which serotonin itself was added to make a concentration of 100 μM for an additional 5 minute incubation. The cells and platelets thusly prepared would then be incubated with the beta carboline, THN, at concentrations of 10 nM to 100 μM. Upon measurement of fluorescent accumulation, saturation would be observed at a THN concentration of approximately 10 μM ($1 \times 10^{-5}$ M) with and $EC_{50}$ value of approximately $2.0 \times 10^{-6}$ M for the cells and platelets together. These values were obtained via extrapolation from pertinent literature on THN and noradrenaline.

Figure 5:
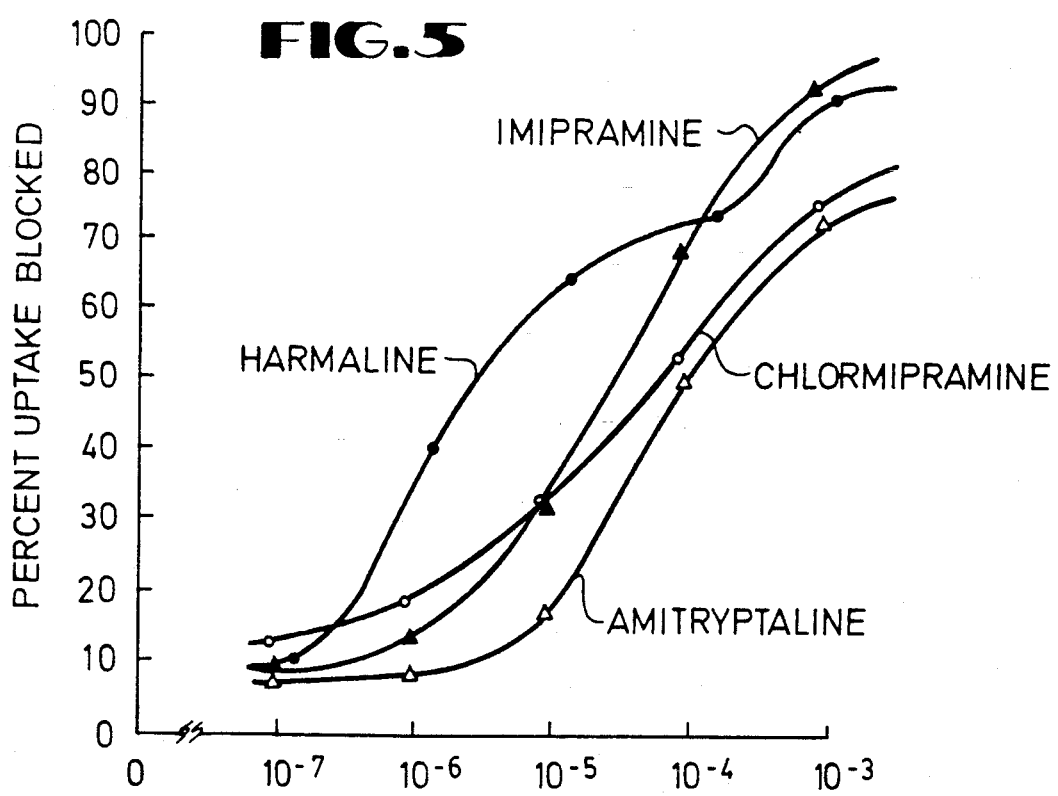
FIG. 5 shows relative inhibitions of $^3$[H] serotonin uptake in retina by tricyclic antidepressants and harmaline.

As shown in FIG. 5, the uptake of $^3$H-serotonin by retina is competitively inhibited by harmaline as well as antagonized by imipramine, chlormipramine and amitryptaline.

Another aspect of the present invention is generally directed to a method for evaluating the functioning of a neurotransmitter system in mammals. The inventive method generally includes the steps of:

a. adding a quantity of a beta carboline to a mammalian tissue sample with a functioning neurotransmitter system, said beta carboline accumulating in the functioning neurotransmitter system of said sample; and b. fluorescently imaging the sample, wherein areas of concentrated fluorescence correspond to reservoirs of beta carboline accumulated by the functioning neurotransmitter system.

Tests of the present invention have determined that both the rate and quantity of the beta carboline taken up into the neurotransmitter system are indicative of the functioning of this transport system.

The rate of velocity of a reaction, (here, the rate of uptake of the beta carboline), may be obtained by measuring the reaction (the accumulation of the beta carboline) at various time intervals of exposure to various concentrations of substrate. These measurements may be used to construct a graph of effect (beta carboline accumulation) over time. The Vmax (maximum velocity) of such a reaction may be determined and is related to the activity of that process according to the fundamentals of Michaelis-Menton enzyme analysis.

In support of the hypothesis that beta carboline accumulation is mediated by active, living mechanisms rather than passive, non-specific attachment, a number of experiments were performed. Active transport of neurotransmitters across the membrane of cells is an energy and sodium dependent phenomena. Tests of the accumulation of beta carboline found it to indeed be both energy and sodium dependent. According to one test of the present inventive method, it was determined that incubating the tissue in sodium-free or cold buffer drastically changed the uptake of beta carboline by the uptake sites of the neurotransmitter system as is characteristic of amine membrane transport systems.

According to one preferred embodiment, the beta carboline is used to determine the functioning of a neurotransmitter system in human tissue. It is believed that this method will be useful in clinically evaluating the psychopharmaceutical needs of a patient in need thereof. According to the invention method, the rate and quantity of beta carboline accumulated in a neurotransmitter system is indicative of how effectively the neurotransmitter system is functioning in the individual in question.

The present inventive method should be beneficial in determining those individuals who would benefit from psychopharmacological therapy, since it is only those patients who have a defect in a neurotransmitter system who benefit from such therapy.

Therefore, a further aspect of the present invention is directed to a method of selecting and predicting the effectiveness of a proposed psychopharmacologic agent interacting with a neurotransmitter system in an individual, the method comprising the steps of:

a. adding to a tissue sample from an individual, neurotransmitter agonists or antagonists which block undesired localization of beta carboline;

b. interacting the sample with a proposed or standardized psychopharmacologic agent used to affect the neurotransmitter system;

c. adding a quantity of a beta carboline which accumulates in the neurotransmitter system;

d. fluorescently imaging the tissue sample, wherein areas of concentrated fluorescence correspond to reservoirs of beta carboline accumulated; and e. comparing beta carboline images to those obtained from a tissue sample obtained when step (b) is omitted.

According to the method, the undesired localization of the beta carboline in the tissue sample is blocked so that a select neurotransmitter system may be studied. This is advantageous since the therapeutic action of several of the psychopharmaceutical agents is generally derived from the interaction with only one neurotransmitter system. The undesired localization of the beta carboline in the tissue sample is blocked by adding an antagonist to the sample which antagonizes and blocks the interaction of the beta carboline with the neurotransmitter systems not being studied. The psychopharmaceutical and the beta carboline are subsequently interacted with the tissue sample. Preferably, the selected beta carboline interacts with the neurotransmitter system in a manner which is similar to the neurotransmitter which corresponds to the neurotransmitter system. Therefore, by examining the effect that the psychopharmaceutical has on the uptake and storage of the beta carboline, the effect that the psychopharmaceutical has on the corresponding neurotransmitter may be extrapolated. This interaction may be studied by fluorescently imaging the sample. Areas of concentrated fluorescence corresponding to reservoirs of beta carboline accumulated by the neurotransmitter system. As discussed above, the rate and quantity of the beta carboline accumulated in the neurotransmitter system is indicative not only of the functioning of the neurotransmitter system, but also of the effectiveness of the psychopharmaceutical in altering the functioning of the neurotransmitter system. This ability to determine a particular psychopharmaceutical'effect on a select neurotransmitter system is advantageous since this would be useful in identifying potential nonresponders to a particular agent. Further, by comparing studies on the same individual before and after administration of the psychopharmaceutical agent, an overall determination may be made as to the effectiveness of a particular psychopharmaceutical, or potential effectiveness, on the particular pathology of that individual. A still further advantage is realized by interacting the tissue sample with various dosages of the psychopharmaceutical agent, and comparing those results to determine the most effective dosage for that particular patient.

While the invention is susceptible to various modifications and alternative forms, specific embodiments thereof have been shown by way of example, in the drawings and will have been herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

Citations in the following list are incorporated in pertinent part by reference herein for the reasons cited in the text.

REFERENCES

Airaksinen, M. M., A. Lrvklin, V. Saano, L. Tuomisto, and J. Gynther (1987) Tremorigenic effect and inhibition of tryptamine and serotonin receptor binding by beta-carbolines. Pharmacol. and Toxicol. 60, 5.

Airaksinen, M. M., V. Saano, E. Steidel, H. Juvonen, A. Huhtikangas and J. Gynther (1984) Binding of beta-carbolines and tetrahydroisoquinolines by opiate receptors of the deltatype. Acta pharmacol. et toxicol. 55, 380.

Airaksinen, M. M., B. T. Ho, R. An. D. Taylor (1978a) Major pharmacological effects of 6-methoxytetrahydro-beta-carboline, a drug elevating the tissue 5-hydroxytryptamine level. Arzneimittelforsch. 28, 42.

Airaksinen, M. M., J. T. Huang, B. T. Ho, D. Taylor and K. Walker (1978b) The uptake of 6-methoxy-1,2,3,4-tetrahydro-beta-carboline and its effect on 5-hydroxytryptamine uptake and release in blood platelets. Acta pharmacol. et toxicol. 48, 375.

Airaksinen, M. M. and I. Kari (1981) Beta-Carbolines, psychoactive compounds in mammalian body. Part I: occurrence, origin and metabolism. Med. Biol. 59, 21.

Airaksinen, M. M. and I. Kari (1981b) Beta-Carbolines, psychoactive compounds in mammalian body. Part II: effects. Med. Biol. 59, 190.

American Medical Association. (1989). *Drug Evaluations 6th Edition*, American Medical Association, Chicago.

Binkley, S., M. Hryshchyshyn and M. Reilly (1979) NAT responds to environmental lighting in the eye as well as in the pineal gland. Nature 281, 479.

Binkley S., K. B. Reilly and M. Hryshchyshyn (1980) N-acetyltransferase in the chick retina. I. Circadian rhythms controlled by environmental lighting are similar to those in the pineal gland. J. Comp. Physiol. Biochem. Syst. Environ. Physiol. 139, 103.

Blackwell, B. (1981) Adverse effects of antidepressant drugs. Part 1. Monoamine oxidase inhibitors and tricyclics. Drugs 21, 201.

Bosin, T. R., Jarvis, C. A. (1985) Derivation in aqueous solution, isolation and separation of tetrahydrobetacarbolines and their precursors by liquid chromatography. J. Chromatogr. 341, 287.

Briley, M. S., R. Raisman, and S. Z. Langer (1979) Human platelets possess high-affinity binding sites for $^3$H-imipramine. Eur. J. Pharmacol. 58, 347.

Briley, M. S., S. Z. Langer, R. Raisman, et al. (1980) Tritiated imipramine binding sites are decreased in platelets of untreated depressed patients. Science 209, 303.

Bruning, G. and H. Rommelspacher (1985) Solubilization of high-affinity [$^3$H]tryptamine-binding sites from rat brain. Eur. Biochem. 153, 95.

Burkard, W. P. and Kettler, R. (1977) Harmaline and its sulphur analogue: Increase of cerebellar cyclic GMP and inhibition of monoamine oxidase. Biochem. Pharmacol. 26, 1303.

Canessa M., E. Jaimovich and M. de la Fuente (1973) Harmaline: a competitive inhibitor of Na+ ion in the (Na+ − K+)-ATPase system. J. Membrane Biol. 13, 263.

Cardinali, D. P. and J. M. Rosner (1971) Retinal localization of the hydroxyindole-0-methyltransferase (HIOMT) in the rat. Endocrinology 89, 301.

de la Torre, J. C. and J. W. Surgeon (1976) A methodological approach to rapid and sensitive monoamine histofluorescence using a modified glyoxylic acid technique: the SPG method. Histochem. J. 49, 81.

Deulofeu, V.; *Ethnopharmacologic Search for Psychoactive Drugs*. U.S. Government Printing Office, 393.

Erecinska, M. (1987) The neurotransmitter amino acid transport systems. Biochemical Pharmacology 36, 3547.

Fuentes, J. A. and V. G. Longo. (1971) An investigation on the central effects of harmine, harmaline, and related B-carbolines. Neuropharmacology 10:15–23.

Fuller, R. W. (1976) The rise and fall of MTHF as a methyl donor in biogenic amine metabolism, Life Sci. 19, 625.

Fuller, R. W., C. J. Wong and S. K. Hemrick-Luecke (1986) MD 240928 and harmaline: opposite selectivity in antagonism of the inactivation of types A and B monoamine oxidase by pargyline in mice. Life Sci. 38, 409.

Gershon, S. and W. J. Lang. (1962) A psycho-pharmacological study of some indole alkaloids. *Archs Int. Pharmacodyn. Ther.* 135:31–56.

Given, M. B. and G. L. Longenecker (1983) Tetrahydroisoquinolines and beta-Carbolines: specific binding to human platelet alpha$_2$-receptors in vivo Research Communications in Chemical Pathology and Pharmacology 41, 8.

Glennon, R. A. and P. K. Gessner (1979) Serotonin receptor binding affinities of tryptamine analogues. J. Med. Chem. 22, 28.

Glennon, R. A. (1981) Serotonin receptor interactions of harmaline and several related beta-carbolines. Life Sci. 29, 861.

Hsu, L. L. and A. J. Mandell (1975) Res. Commun. Chem. Pathol. Parmacol. 12, 355.

Inoue, S., Tokuyama, T., Takai, K. (1983) Picomole analyses of tryptophan by derivatization to 9-hydroxymethyl beta carboline. Anal. Biochem. 132, 468.

Iuvone, P. M. and J. C. Besharse (1983) Regulation of indoleamine N-acetyltransferase activity in the retina: Effects of light and dark, protein synthesis inhibitors and cyclic nucleotide analogues. Brain Res. 273, 111.

Langer, S. Z., R. Raisman, L. Tahraoui, B. Scatton, R. Niddam, C. R. Lee, and Y. Claustre (1984) Substituted tetrahydro-beta-carbolines are possible candidates as endogenous ligands of the [$^3$H]-imipramine recognition site. Eur. J. Pharmacol. 98, 153.

Leonard, B. E. (1988) Pharmacological effects of serotonin reuptake inhibitors. J. Clin. Psychiatry 49, 8.

Mandel, L. R., A. Rosegay, R. W. Walker and W. J. A. VandenHeuvel (1974) 5-Methyltetrahydrofolic acid as a mediator in the formation of pyridoindoles. Science 186, 741.

Marcusson, J. O., I. T. Backstron and S. B. Ross (1986) Single-site model of the neuronal 5-hydroxytryptamine uptake and imipramine-binding site. Molec. Pharmacol. 30, 121.

McKenna, D. J., G. H. Towers and F. Abbott (1984) Monoamine oxidase inhibitors in South American hallucinogenic plants: tryptamine and beta-carboline constituents of ayahuasca. J. Ethnopharmacol. 10, 195.

Mitchell, C. K. and D. A. Redburn (1985) Analysis of pre- and postsynaptic factors of the serotonin system in rabbit retina. J. Cell. Biol. 100, 64.

Muller, W. E., K. J. Fehske, H. D. Borbe, U. Wollert, C. Nanz and H. Rommelspacher (1981) On the neuropharmacology of harmane and other beta-carbolines. Pharmacol. Biochem. Behav. 14, 693.

Osborne, N. N. (1980) In vitro experiments on the metabolism, uptake, and release of 5-hydroxytryptamine in bovine retina. Brain Res. 184, 283.

Pang, S. F., G. M. Brown, L. J. Grota, J. W. Chambers and R. L. Rodman (1977) Determination of N-acetylserotonin and melatonin activities in the pineal gland, retina, harderian gland, brain and serum of rats and chickens. Neuro endocrinology 23, 1.

Paul, S. M., M. Rehavi, P. Skolnick and F. K. Goodwin (1980) Demonstration of specific high affinity binding sites for $^3$H-imipraimin on human platelets. Life Sci. 27. 953.

Paul, S. M., M. Rehavi, K. C. Rice, et al. (1981a) Does high affinity $^3$H-imipramine binding label serotonin reuptake sites in brain and platelet. Life Sci. 28, 2753.

Paul, S. M., Rehavi, P. Skolnick, et al. (1981b) Depressed patients have decreased binding of tritiated imipramine to platelet serotonin transporter. Arch. Gen. Psychiatry 38, 1315.

Redburn, D. A. and L. Churchill (1987) An indoleamine system in photoreceptor cell terminals of the Long-Evans rat retina. J. Neurosci. 7, 319.

Rodieck, R. W. (1973) *The Vertebrate Retina,* W. H. Freeman, San Francisco.

Rommelspacher, H., S. M. Strauss and K. Rehse (1978) Beta-carbolines: A tool for investigating structure-activity relationships of the high-affinity uptake of serotonin, noradrenaline, dopamine, GABA, and choline into a symaptosome-rich fraction of various parts from rat brain. J. Neurochem. 30, 1573.

Rommelspacher, H., S. M. Strauss and J. Lindemann (1980) Excretion of tetrahydroharmane and harmane into the urine of man and rat after a load with ethanol. FEBS Lett. 109, 209.

Rommelspacher, H., C. Nanz, H. O. Borbe, K. J. Fehske, W. E. Muller and U. Wollert (1981) Benzodiazepine antagonism by harmane and other beta-carbolines in vitro and in vivo. Eur. J. Pharmacol. 70, 409.

Rommelspacher, H., H. Damm, S. Strauss and G. Schmidt (1984) Ethanol induces an increase of harmane in the brain and urine of rats. Naunyn-Schmiedegerg's Arch. Pharmacol. 327, 107.

Rommelspacher, H., G. Bruning, R. Susilo, M. Nick & R. Hill (1985) Pharmacology of harmalan (1-3,4-dihydro-betacarboline) Eur. J. Pharmacol. 109, 363.

Schoenenweid F., W. Durand-Arczynska and J. Durand (1986) Effects of harmaline on ion transport and oxygen consumption by the bovine tracheal epithelium. J. Physiol. Paris 81, 19.

Schultes, R. E. and A. Hofmann (1973) *The Botany and Chemistry of Hallucinogens,* Charles C. Thomas, Springfield.

Schultes, R. E. and A. Hofmann (1979) *Plants of the Gods,* McGraw-Hill Book Co., New York.

Sepulveda F. V., J. W. L. Robinson (1974) Harmaline, a potent inhibitor of sodium-dependent transport. Biochim. Biophys. Acta 373, 527.

Sklar, L. A., D. A. Finney, Z. G. Oades, A. J. Jesaitis, R. G. Painter, and C. G. Cochrane. (1984) The Dynamics of Ligand-Receptor Interactions. *J. Biol. Chem.* 249:5661–5669.

Smith, M. D. and P. C. Parker (1974) The maturation of indolamine metabolism in the lateral eye of the mouse. Comp. Biochem. Physiol. 49A, 281.

Sneddon, J. M. (1969) Sodium-dependent accumulation of 5-hydroxytryptamine by rat blood platelets. Br. J. Pharmacol. 37, 680.

Sneddon, J. M. (1979) A relationship between internal Na+/K+ and the accumulation of $^{14}$C-5-hydroxytryptamine by rat platelets. Br. J. Pharmacol. 43, 834.

Sneddon, J. M. (1973) Blood platelets as a model for monoamine-containing neurons. Prog. Neurobiol. 1, 151.

Stahl, S. M. (1985) Peripheral models for the study of neurotransmitter receptors in man. Psychopharm. Bull. 21, 664.

Stanley, M., J. Virgilio and S. Gershon (1982) Tritiated imipramine sites are decreased in the frontal cortex of suicides. Science 216, 1337.

Steinkamp, J. A. and P. M. Kraemer. (1979) Flow Cystometry and Sorting. John Wiley and Sons, NY, pp. 497–504.

Susilo, R. and H. Rommelspacher (1987) Formation of a b-carboline (1,2,3,4-tetrahydro-1-methyl-b-carboline-1-carboxylic acid) following intracerebroventricular injection of tryptamine and pyruvic acid. Naunyn-Schmiedeberg's Arch. Pharmacol. 335, 70.

Thomas T. N. and D. A. Redburn (1979) 5-Hydroxytryptamine —A neurotransmitter of bovine retina. Exp. Eye Res. 28, 55.

Titus J. A. S. A. Sharrow J. M. Connolly and D. M. Segal. (1981) *Proc. Natl. Acad. Sci. U.S.A.,* 78:519,523.

Wyatt, R. J., E. Erdelyi, J. R. DoAmaral, G. R. Elliott, J. Renson and J. D. Barchas (1975) Tryptoline formation by a preparation from brain with 5-methyl tetrahydrofolic acid and tryptamine. Science 187, 853.

Wiechmann, A. F., D. Bok and J. Horowitz (1985) Localization of hydroxyindole-0-methyltransferase in the mammalian pineal gland and retina. Invest. Ophthalmol. Vis. Sci. (Suppl.) 26, 253.

Wirz-Justice, A. (1988) Platelet research in psychiatry. Experimentia 44, 145.

What is claimed is:

1. A method for evaluating a serotonin uptake system in mammalian platelet or monocyte tissue as a measure of specific harmaline fluorescence of serotonin uptake sites, the method comprising the steps of:

preincubating a control sample and a test sample of the platelet or monocyte tissue with an α-2 inhibitor;

adding harmaline to the preincubated test sample;

fluorescently imaging the control sample and the test sample to determine specific harmaline fluorescent localization at serotonin uptake sites; and comparing the amount of fluorescence in the test tissue to the amount of fluorescence in the control tissue, wherein the difference between the fluorescence in the control tissue and the test tissue is a measure of the serotonin uptake system of the mammalian platelet or monocyte tissue.

2. The method of claim 1 wherein the α-2 inhibitor is yohimbine.

* * * * *